US007816138B2

(12) United States Patent
Dutra

(10) Patent No.: US 7,816,138 B2
(45) Date of Patent: *Oct. 19, 2010

(54) BIOREACTOR SYSTEM AND METHOD FOR THE PRODUCTION AND COLLECTION OF BLOOD CELLS FROM ENGINEERED BONE MARROW TISSUE

(75) Inventor: Timothy F. Dutra, 14689 Fieldstone Ct., Saratoga, CA (US) 95070

(73) Assignee: Timothy F. Dutra, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/329,441

(22) Filed: Dec. 5, 2008

(65) Prior Publication Data

US 2009/0104698 A1    Apr. 23, 2009

Related U.S. Application Data

(62) Division of application No. 11/375,178, filed on Mar. 13, 2006, now Pat. No. 7,476,541.

(60) Provisional application No. 60/666,659, filed on Mar. 29, 2005.

(51) Int. Cl.
*C12N 5/02* (2006.01)
(52) U.S. Cl. .................................. 435/383; 435/289.1
(58) Field of Classification Search ....................... None
See application file for complete search history.

(56) References Cited

U.S. PATENT DOCUMENTS 7,476,541 B1 *  1/2009  Dutra ......................... 435/394
7,494,811 B2 *  2/2009  Wolfinbarger et al. ....... 435/373

* cited by examiner

*Primary Examiner*—James S Ketter
(74) *Attorney, Agent, or Firm*—Fenwick & West LLP

(57) ABSTRACT

Methods and apparatus for a bioreactor system for growing cells are provided. The bioreactor system includes a reaction chamber for cultivating harvested tissue in a culture medium, and a hydrodynamic apparatus connected to the reaction chamber that generates a cyclic negative pressure differential in the bioreactor. Additionally, the apparatus includes a collection enclosure for collecting cells produced by tissue in the reaction chamber. Also encompassed are embodiments for harvesting and preparing cells and tissue sections, combining the cells and the tissue sections in a culture medium to cultivate tissue, maintaining the tissue under conditions that permit production of cell products, applying cyclic negative pressure to the culture over a period of time, and collecting cell products discharged. Further disclosed are embodiments for placing harvested tissue and cells in a diffusion chamber, creating an oscillating negative pressure differential in the bioreactor over a period of time, and collecting the cell products.

23 Claims, 7 Drawing Sheets

BIOREACTOR SYSTEM AND METHOD FOR THE PRODUCTION AND COLLECTION OF BLOOD CELLS FROM ENGINEERED BONE MARROW TISSUE

RELATED APPLICATIONS

This application is a divisional of U.S. patent application Ser. No. 11/375,178, filed on Mar. 13, 2006, entitled "A Bioreactor System And Method For The Production And Collection Of Blood Cells From Engineered Bone Marrow Tissue," which claims the benefit of U.S. Provisional Application No. 60/666,659, filed on Mar. 29, 2005, entitled "A Bioreactor System And Method For The Production And Collection Of Blood Cells From Engineered Bone Marrow Tissue," the entire disclosures of which are both hereby incorporated by reference herein in their entireties for all purposes.

BACKGROUND OF THE INVENTION

1. Field of the Invention

The present invention relates to methods and apparatus for tissue engineering using a bioreactor system. More particularly, the invention relates to producing and collecting blood cells in a bioreactor system environment that re-creates the pressure differential between the tissue interstitial pressure and the outflow capillary and venular pressure.

2. Description of the Related Art

Shortages of red blood cells for transfusion can delay elective surgeries, and even affect disposition of trauma center triage. Since originally conceptualized by Trentin (1970), the blood-forming microenvironment has become understood as the necessary tissue niche inductive of blood cell production by blood stem cells. Tissue engineering offers a potential solution to the blood cell shortage problem by taking advantage of progenitor or stem cells located in bone marrow. Stem cells in the marrow of the body's longest bones are continuously at work to meet the body's varying demand for billions of new blood cells a day. Tissue engineering techniques can potentially be used to produce red blood cells, white blood cells, and/or blood platelets, through sampling of bone marrow stroma, isolating of progenitor cells, multiplying of the cells until a sufficient cell number is obtained, and seeding of the cells onto scaffolds. By cultivating this tissue in a bioreactor system, it is possible to provide local environmental conditions that will encourage the cells to differentiate in a particular direction (i.e., differentiate into blood cells). Additionally, stem or progenitor cells for some cell or tissue lineages, including hematopoietic, can be collected from peripheral blood by apheresis with minimal discomfort to the blood donor compared to bone marrow harvest. While tissue engineering is potentially a very beneficial solution to blood cell shortages, mastering tissue-engineering techniques that will successfully result in production of red blood cells is a challenge that is still far from being resolved.

One problem is creating the appropriate design of bioreactor systems for blood cell production. The rational design of bioreactor systems for blood cell production is being discussed in current biomedical scientific articles (Cabrita et al., 2003; Noll et al., 2002; and Nielsen, 1999). Three-dimensional systems for extracorporeal blood cell production have been reported on nylon mesh (Naughton et al., 1991), in hollow fibers (Rice et al., 1994), and on porous microspheres (Mantalaris et al, 1998), as well as in sterilized spongy (marrow cavity) bone (Januszewski et al, 2003). However, these bioreactor systems do not allow red blood cells to be safely and economically cultivated extracorporeally. These bioreactors start with components (e.g., hollow fibers or microspheres) to build upward to cultivate tissue that is engineered to produce blood cells, as opposed to starting at the bone marrow tissue level and deconstructing the tissue into components that can be used to repopulate a three-dimensional bone marrow tissue extracellular matrix.

Current bioreactor systems fail to provide an appropriate environment for production of blood cells. For example, there is currently no effective tissue-cultivation bioreactor system that duplicates the marrow tissue conditions at the tissue level. In most animal tissues, the interstitial fluid outflow of the extravascular space is into capillaries of the arteriovenous and lymphatic vascular systems, and mostly to the former.

In most animal tissues, the interstitial fluid outflow of the extravascular space of tissues, including marrow tissue, is into capillaries of the arteriovenous and in some cases to the lymphatic vascular systems. The capillary network of the arteriovenous system connects to venules or venioles (which are tributaries of the low pressure venous intravascular space), and there is a pulsing or oscillating component of the low-pressure hydrodynamics in the venous intravascular pressure. The current bioreactors fail to recognize or mimic this pressure differential and fail to create realistic tissue conditions as they exist in animal tissues.

Therefore, there is a need for a new approach to bioreactor technology that mimics the realistic tissue conditions existing in animal tissues and that creates a microenvironment that results from interactions of bone marrow-derived connective tissue cells and blood stem cells that are repopulated on and interact within a biochemically complex, three-dimensional bone marrow tissue extracellular matrix. The present invention addresses these and other deficiencies of the prior art as described more fully below.

SUMMARY OF THE INVENTION

Disclosed herein is a bioreactor system for growing cells including a reaction chamber for cultivating harvested tissue in a cell culture medium. The bioreactor system further includes a hydrodynamic apparatus connected to the reaction chamber, and the apparatus generates a cyclic negative pressure differential in the bioreactor system. Additionally, the apparatus includes a collection enclosure for collecting cells produced by the tissue in the reaction chamber.

Accordingly one aspect of the invention is harvesting and preparing cells and tissue sections in a culture to be combined for cultivation, and combining the cells and the tissue sections in a culture medium to cultivate tissue. Another aspect of the invention includes maintaining the tissue under conditions that permit production of cell products. In addition, the invention includes applying cyclic negative pressure to the culture over a period of time, and collecting cell products discharged.

Another aspect of the invention is a bioreactor system for growing cells, which includes a reaction chamber with a diffusion chamber for cultivating tissue, a collection enclosure connected to the diffusion chamber and a hydrodynamic apparatus connected to the reaction chamber. One aspect includes placing harvested tissue and cells in the diffusion chamber in a cell culture medium. Additionally, the invention includes creating an oscillating negative pressure differential between the diffusion chamber and the collection enclosure over a period of time, wherein the oscillating negative pressure differential creates an environment suitable for collection of cell products in the collection enclosure. The invention also includes collecting the cell products in the collection enclosure.

The present invention is defined by the claims, and nothing in this section should be taken as a limitation on those claims.

BRIEF DESCRIPTION OF THE SEVERAL VIEWS OF THE DRAWING

These and other features, aspects, and advantages of the present invention will become better understood with regard to the following description, and accompanying drawings, where.

DETAILED DESCRIPTION OF THE INVENTION

Figure 1:
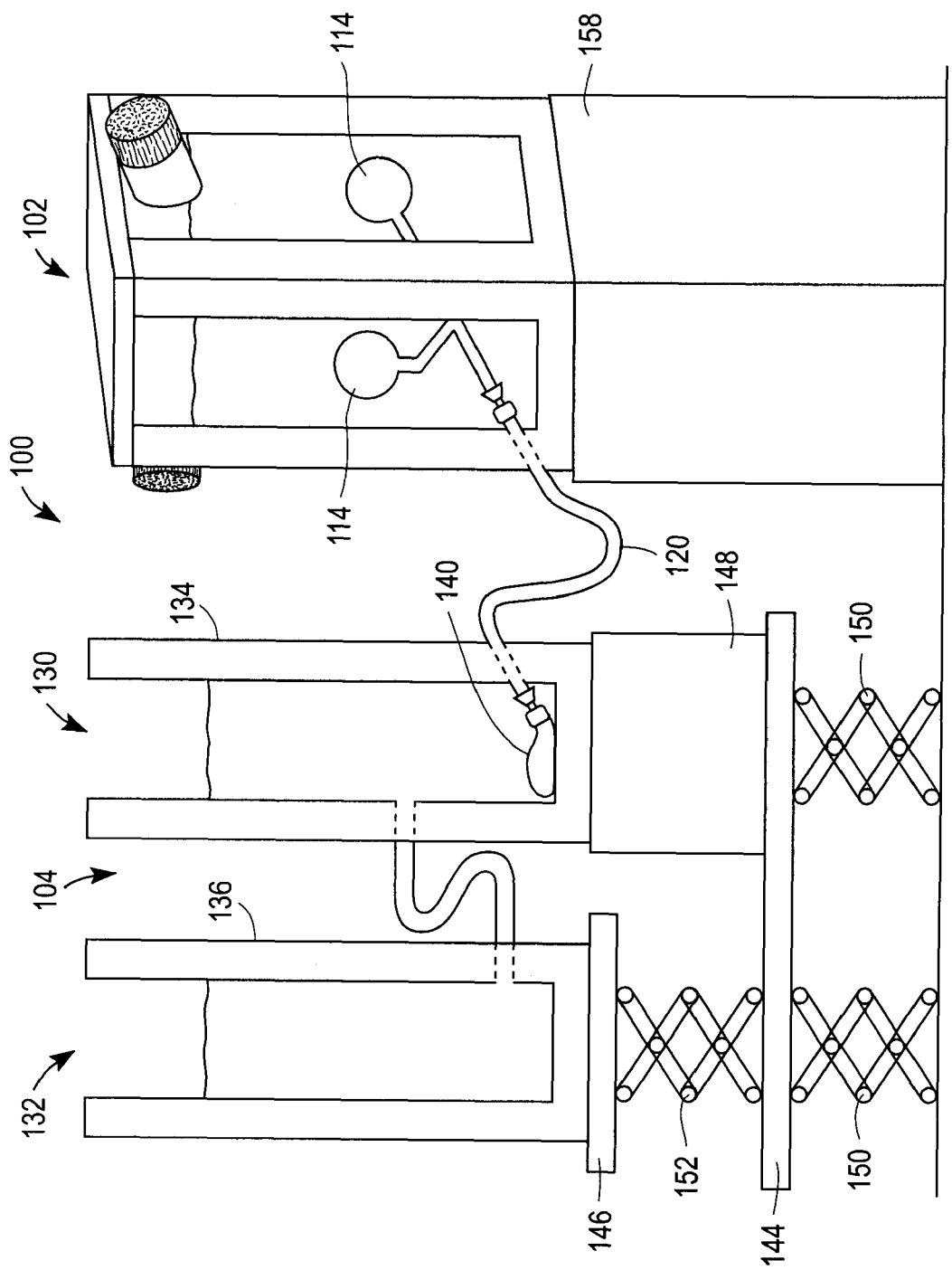
FIG. 1 is a diagram of a bioreactor system for tissue engineering, including a reaction chamber and a hydrodynamic apparatus.

Briefly, and as described in more detail below, described herein are methods and apparatus for tissue engineering using a bioreactor system. The improvements are realized by producing and collecting blood cells in a bioreactor system environment that re-creates the pressure differential between the tissue interstitial pressure and the outflow capillary and venular pressure, and thus facilitates the collection of blood cells. The details of the parameters required to create this cyclic negative pressure and to collect cells are described further within.

Several features of the current approach should be noted. The bioreactor system has two components that are connected by cell collection tubing. One component of the bioreactor system is the reaction chamber, which includes one or more diffusion chambers or diffusion chamber unit cells containing engineered tissue, such as hematopoietic tissue. The other component of the bioreactor system is a hydrodynamic apparatus that creates a cyclic negative pressure differential to harvest and collect in a cell collection enclosure the cells (e.g., blood cells) generated in the reaction chamber. In some embodiments, the cyclic negative pressure differential is composed of two constituent factors: 1) a slow constant negative pressure gradient over a time period (e.g., approximately 24 hours); and 2) a rapidly oscillating negative pressure differential at an approximately constant cycle rate per minute. In some embodiments, the apparatus cycles between 1 and 60 times per minute, while in some embodiments it cycles between 5 and 50 times per minute or 8 and 40 times per minute. In some embodiments it cycles between 10 and 30 times per minute, while in other embodiments it cycles between 15 and 25 times per minute. In some embodiments the cycling occurs over a 48-hour time period (i.e., during a time period of 0 to 48 hours), while in other embodiments, the cycling occurs over a 96-hour time period, a 72-hour time period, a 24-hour time period, a 12-hour time period or a 6-hour time period. In some embodiments, the oscillations of the negative pressure differential occur over range of 10 centimeters of water per minute (i.e., cycling between 0 and −10 centimeters of water), while in some embodiments the oscillations range over 6 centimeters, or 3 centimeters, or 2 centimeters, or 1 centimeter per minute. In some embodiments the overall pressure drop over time is equal to between 1 to 20 centimeters of water, while in other embodiments, the pressure drop is between 2 to 10 centimeters of water or between 3 to 8 centimeters of water or 3 to 6 centimeters, or 4 to 6 centimeters of water. The cyclic negative pressure action facilitates collection of cells.

Advantages of this approach are numerous. One advantage provided by the invention is the development of a bioreactor system that duplicates the marrow tissue conditions at the tissue level. The cyclic negative pressure action facilitates cultivation of blood cells by reproducing the pressure gradient from the tissue interstitium or extravascular pressure (e.g., tissue turgor) to the intravenous or venular capillary system intravascular pressure in the diffusion chambers within the bioreactor reaction chamber. Thus, the system is designed to produce a cyclic (or oscillating) negative pressure differential between the engineered hematopoietic tissue in diffusion chambers in the bioreactor reaction chamber and a blood cell harvest and collection bag housed in a hydrodynamic apparatus.

Another advantage provided by the invention is the development of a bioreactor system that allows cells, such as red blood cells, to be safely and economically cultivated extracorporeally. As one example, the bioreactor system microenvironment can include reciprocal interactions among three cell lineages that include connective tissue or stromal tissue, vessel lining or endothelial tissue, and blood-forming cells or blood stem cells. In this example, the bioreactor system interactions can take place on and in a biochemically complex, three-dimensional extracellular matrix. Rather than starting with cellular components of blood-forming marrow tissue, this example of a method according to the present invention starts with the bone marrow tissue itself, which is deconstructed to remove constituent cellular components, and then the bone marrow tissue extracellular matrix is repopulated to create a functional microenvironment. The invention also can be practiced with other cells, such as, e.g., adult or embryonic stem cells.

The invention is useful for safely and economically cultivating cells within a bioreactor system, such as, e.g., for cultivating mature red blood cells from bone marrow tissue or other progenitor or stem cells.

Definitions

Terms used in the claims and specification are defined as set forth below unless otherwise specified.

The term "in situ" refers to processes that occur in a living cell growing separate from a living organism, e.g., growing in tissue culture.

The term "in vivo" refers to processes that occur in a living organism.

The term "ex vivo" refers to processes of a living organism that are removed from the living organism.

The term "in vitro" refers to processes that occur outside of the living organism in an artificial environment.

The term "mammal" as used herein includes both humans and non-humans and includes but is not limited to humans, non-human primates, canines, felines, murines, bovines, equines, and porcines.

It must be noted that, as used in the specification and the appended claims, the singular forms "a," "an" and "the" include plural referents unless the context clearly dictates otherwise. In addition, ranges recited are intended to be inclusive of the parameters bounding the range unless the context clearly dictates otherwise. For example, a recited range of between one and ten is intended to include one and ten unless the context clearly dictates otherwise.

Structure of the Bioreactor System

Referring to FIG. 1, there is shown a bioreactor system 100 according to one embodiment of the present invention. The bioreactor system 100 has two components, a reaction chamber 102 and a hydrodynamic apparatus 104, which are connected by cell collection tubing 120. During operation, one or both components of the bioreactor system 100 can be maintained in a controlled environment, and preferably within humidified, heated, approximately 3% to 5% $CO_2$ cell culture incubator. In some embodiments, the pressure in the incubator is also controlled.

The reaction chamber 102 includes one or more diffusion chambers 114 or diffusion chamber unit cells containing engineered tissue, such as hematopoietic tissue. The reaction chamber 102 can rest on a block 158 to bring the reaction chamber 102 to approximately the same height as the hydrodynamic apparatus 104.

The hydrodynamic apparatus 104 includes a mechanism for creating oscillations in pressure (e.g., an oscillating apparatus 152) and a collection enclosure or cell collection bag 140 for collecting cells produced in the reaction chamber 102. In some embodiments, the hydrodynamic apparatus 104 includes two components: a collection component 130 and a cyclic component 132. The collection component 130 can include a collection container 134 that contains the cell collection bag 140 for collecting cells produced. The cyclic apparatus 132 can include a cyclic container 136 that rests on an oscillation platform 146 that can be raised and lowered by an oscillation apparatus 152. In some embodiments, the collection container 134 rests on a block 148 that is positioned on a lowering platform 144, and the oscillation mechanism 152 that holds up the oscillation platform 146 and cyclic container 136 also rests on the lowering platform 144. The lowering platform 144 rests on a lowering mechanism 150 that is adapted to lower the cyclic container 136 and the collection container 134 over time. The action of this lowering mechanism in conjunction with the action of the oscillation mechanism create a cyclic negative pressure differential to harvest and collect the cells (e.g., blood cells) in the collection bag 140. The cyclic negative pressure action facilitates collection of cells, and reproduces the pressure gradient from the tissue interstitium to the venular capillary system in the diffusion chambers 114 within the bioreactor reaction chamber 102. The details of the structure of the bioreactor system and its method of operation are discussed below.

Reaction Chamber

Figure 2:
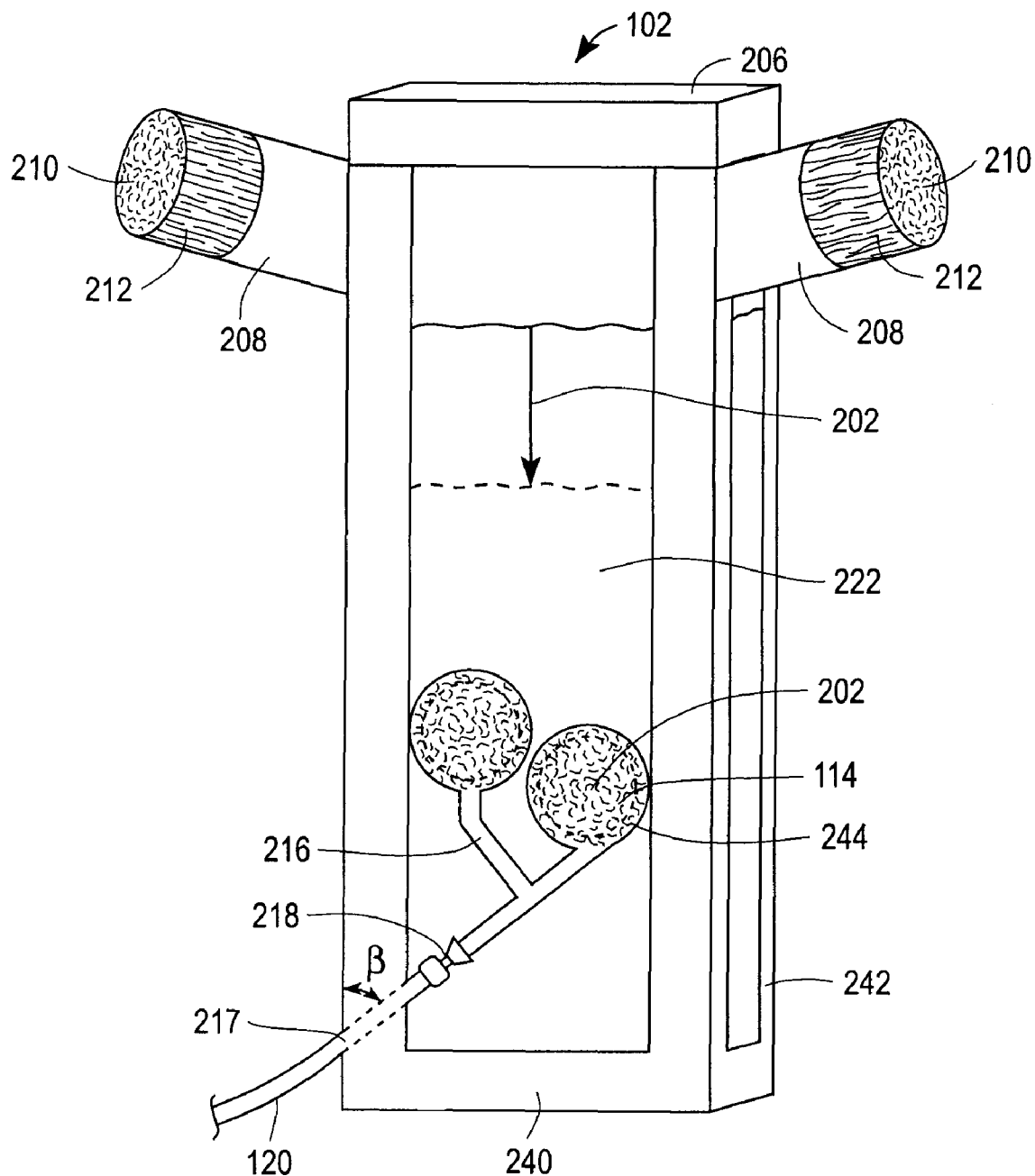
FIG. 2 is a diagram of the reaction chamber in the bioreactor system.

Referring now to FIG. 2, there is shown a reaction chamber 102 according to an embodiment of the present invention. As described above, the reaction chamber 102 includes one or more diffusion chambers 114 containing engineered tissue. The contents of the reaction chamber 102 are generally sterile or substantially sterile. The reaction chamber 102 can be rectangular in shape with the long axis vertical as shown in FIG. 2, or the reaction chamber can be another suitable shape, such as square, cylindrical, etc. The reaction chamber 102 shown in FIG. 2 is a rectangular structure that includes four walls (a front wall 240, a left side wall 242, a back wall (not shown) and a right side wall (not shown)), a base panel (not shown), and a top panel 206, resulting in the contents of the chamber 102 being enclosed on all sides.

The reaction chamber 102 can be any suitable size and have walls of any thickness suitable for containing the culture medium therein and the diffusion chambers 114 for cultivation of tissue. The reaction chamber 102 is constructed of a suitable biocompatible material, such as a plastic or glass, and preferably the reaction chamber is constructed of a thick polycarbonate plastic. In some embodiments, the reaction chamber 102 walls are approximately ⅜ inches thick, and the chamber 102 is a rectangular enclosure measuring approximately 4×6×16 centimeters with internal dimensions of approximately 2×4×14 centimeters. Thus, in the embodiment shown in FIG. 2, the front wall 240 and back wall (not shown) could be approximately 6 cm. in length (4 cm. in internal length) and 16 cm. in height (14 cm. in internal height), the left side wall 242 and right side wall (not shown) could be 4 cm. in length (2 cm. in internal length) and 16 cm. in height (14 cm. in internal height). The measurements of the base panel (not shown) and top panel 206 would be approximately 4×6 cm. (2×4 cm. internally) in these embodiments. Additionally, in these embodiments, the chamber 102 has an approximate volume of 112 cc, and the long axis of the reaction chamber 102 is vertical when in operation.

At the beginning of an operational run, the reaction chamber 102 contains sterile cell culture medium 222, preferably approximately 95 cc, though the reaction chamber can contain any volume suitable for the procedure. The reaction chamber can be constructed so that the top panel 206 of the reaction chamber 102 is removable for the placement, with sterile technique, of the diffusion chambers 114 containing engineered tissue. In some embodiments, the reaction chamber 102 also has attached canted ports 208, such as flask necks that can be screw-sealed with caps 212 constructed of plastic or another suitable material. These types of screw-seal caps 212 can be purchased from various vendors, such as B-D SCIENTIFIC® or others. The tops of these plastic caps can be open, but are typically covered by a porous material 210, such as a hydrophobic microporous (e.g., 0.2 micron pore size) membrane of nylon-coated acrylic polymer (e.g., USP Class 6). This porous material 210 allows the reaction chamber 102 gas exchange to occur during an operational run, while preventing microbial contamination of the contents when the canted ports 208 are screw-sealed.

In its construction, the reaction chamber 102 includes an opening 217 through which the one or more diffusion chambers 114 are connected to the hydrodynamic apparatus 104. In the embodiment shown in FIG. 2, this opening 217 is in the lower portion of the reaction chamber 102 at an angle β from the horizontal that is preferably equal to approximately 45 degrees. However, the opening 217 can be located elsewhere on the reaction chamber 102 and angle β can be larger or smaller as suitable. In some embodiments, this opening 217 is constructed to be slightly wider in diameter than the outside diameter of standard intravenous tubing (e.g., o.d. 0.142 inch).

During construction and assembly, cell collection tubing 120 is attached to the one or more diffusion chambers 114, and this tubing 120 runs through the opening 217 in the reaction chamber 102 at angle β and outside of the reaction chamber 102 to connect to the hydrodynamic apparatus 104. The cell collection tubing 120 can be standard intravenous tubing with an end that is factory-sealed by a rubber-covered injection port 218 or some other type of port (e.g., a port capped with some other injectable seal, such as synthetic polyisoprene). The cell collection tubing 120 can also be sealed to the wall of the opening 217 with epoxy glue or another biocompatible adhesive or sealing mechanism.

The diffusion chambers 114 each include an outer ring 244 as illustrated in FIG. 2 by the dotted line. A porous covering 202 (e.g., a filter, a membrane, etc.) is attached to each side of the ring 244. In some embodiments, the ring 244 and porous covering 202 (e.g., 0.4 micron pore size) are purchased as unassembled diffusion chambers from a vendor (e.g., MIL-LIPORE™). For example, vendor designed rings 244 can be purchased in which the rings 244 are constructed of PLEXI-GLAS® with a 0.59 mm side hole, and the porous covering 202 can be a 13 mm diameter PVDF filter disc with 0.45 micron pore size or a 13 mm diameter cellulose ester filter disc with a 0.45 micron pore size. In some embodiments, the filter disc pore size is larger or smaller, as suitable. The porous covering 202 forms an open space or chamber that is bounded by the outer ring 244 and the porous covering 202 on either side of the outer ring 244, and this chamber can house tissue for cultivation Prior to assemblage of each of the diffusion chambers 114, a single exit hole or port in the side of the ring 244 is connected by epoxy glue or some other type of adhesive or connection mechanism to connective tubing 216 (e.g., standard intravenous tubing, such as PVC with DEHP, i.d. 0.103 and o.d. 0.142 inch). In some embodiments, there are more than one connector tubing 216 segments, one for each diffusion chamber 114. The connector tubing 216 segments can be attached to the two diffusion chamber rings 244 and can be connected to each other by a "Y" connector. In some embodiments, the "Y" connector includes a standard syringe-type Luer lock nozzle forming the base or vertical arm of the "Y" connector, so that diffusion chambers 114 are connected by tubing to each of the two upward arms and the Luer lock nozzle is directed downwards.

Prior to each operational run, the reaction chamber 102 and the diffusion chamber 114 assemblage are sterilized (e.g., by exposure to ethylene oxide gas, gamma irradiation, or another suitable sterilization method), and kept in sterile packaging. After assembling and loading the diffusion chambers 114 with engineered hematopoietic tissue, as described below, the porous coverings 202 of the diffusion chambers 114 are sealed to the outer rings 244 (e.g., with epoxy glue or another sealing mechanism, or according to the diffusion chamber vendor's product directions). In some embodiments, a large bore sterile needle (e.g., 18 to 14 gauge) is attached to the Luer lock nozzle on the vertical arm of the "Y" connector connecting two diffusion chambers 114. The loaded and sealed diffusion chamber 114 assemblage is then placed, "Y" connector downwards, into the reaction chamber 102, and the large bore needle (not shown) is driven into the rubber-covered injection port 218 on the cell collection tubing 120 exiting the side of the base of the reaction chamber 102. As will be described in more detail below, cell culture medium 222 is added to the reaction chamber 102. In some embodiments, the medium 222 is added to a height of 12 centimeters (approximately 95 cc.), which is 3 to 6 centimeters above the level of the diffusion chambers 114. This height of the cell culture medium 222 will prevent air exposure of the diffusion chambers as the level of the medium subsides over the course of the operational run. The top panel 206 of the reaction chamber 102 and the side screw cap canted ports 208 of the reaction chamber 102 are sealed for the operational run. As will be described in more detail below, the cell culture medium 222 fluid level will decrease during the operational run, and this is depicted by arrow 204. In some embodiments, the fluid level will decrease by approximately 3 cm in height, but in other embodiments, the fluid level drops by another amount greater than or less than 3 cm. In some embodiments, during an operational run, the height of the medium in the reaction chamber 102 is restored by medium introduced from a reservoir (not shown) attached to the reaction chamber, or by access via one of the canted ports 208, or by other means, as suitable.

Hydrodynamic Apparatus

Figure 3:
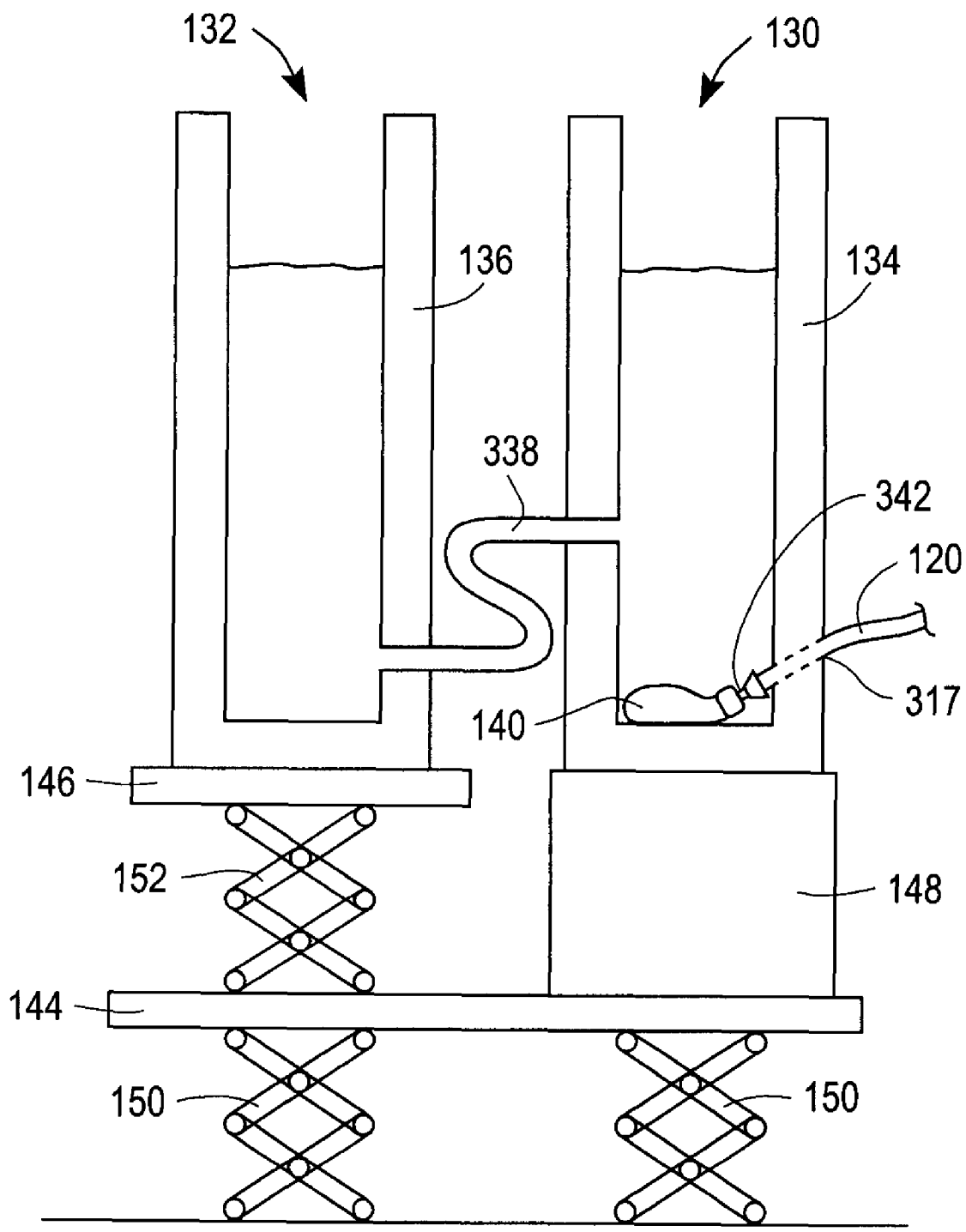
FIG. 3 is a diagram of the components of the hydrodynamic apparatus at the start of the cell collection time period.

Referring now to FIG. 3, there is shown the hydrodynamic apparatus 104 according to an embodiment of the present invention. As described previously, the hydrodynamic apparatus 104 can include two components, the collection component 130 and the cyclic component 132. The collection component 130 includes a collection container 134, and the cyclic component 132 includes a cyclic container 136. These containers 134, 136 can be beakers, flasks, test tubes, or other suitable containers or combinations of container types for holding fluids. The containers 134, 136 can be various shapes (e.g., cylindrical, rectangular, square, etc.) and various sizes, and the containers 134, 136 can be constructed of various different types of materials (e.g., glass, plastic, etc.), but are preferably constructed of polycarbonate plastic, similar to the construction of the reaction chamber 102. The containers 134 and 136 are typically filled with a liquid (e.g., water, cell culture medium, etc.) up to a certain height. For example, in some embodiments the containers 134, 136 are either glass or plastic beakers that are 18 centimeters in height and are filled to 12 centimeters in height with water or cell culture medium. In some embodiments, the two containers 134 and 136 are constructed of two different types of materials, are different sizes and/or shapes, and are filled with different liquids at different heights.

In the embodiment shown in FIG. 3, the collection container 134 houses the cell collection bag 140 and facilitates its function for the harvest of cells grown in the diffusion chambers 114, which are shed into the cell collection tubing 120 from the engineered tissue loaded into the diffusion chambers 114. The collection bag 140 can be constructed of various types of materials (e.g., plastic, rubber, cellulose, polyvinylidene difluoride, etc) and can be any size or shape suitable for collection of cells in the bioreactor system 100. Depending upon the method selected for cell harvest, the collection bag 140 may be either permeable or semi-permeable to dissolved gases or the collection bag 140 may be impermeable. As an example of a permeable or semi-permeable collection bag, the cell collection bag 140 can be a commercially obtained sterile dialysis tubing (e.g., cellulose ester or polyvinylidene difluoride) that may be purchased from a vendor. As an example of an impermeable collection bag, the cell collection bag 140 can be a commercially obtained intravenous solution mini-bag that can be purchased from a vendor with either 25 or 50 milliliters of sterile normal saline, and can have a factory-sealed rubber-covered injection port 342. This intravenous solution mini-bag can also have a second port, which is a female connector (not shown) for attachment of the male connector or "spike" of a connector for intravenous tubing.

In some embodiments, the containers 134, 136 are constructed with top panels (not shown) so that the contents can be maintained generally sterile or substantially sterile. In these embodiments, the top panels (i.e., similar to panel 206 shown in FIG. 2) of the containers 134, 136 are removable for the placement, with sterile technique, of a permeable or semi-permeable collection bag 140 and cell culture medium in both the collection container 134 and in the cyclic container. In some embodiments, the containers 134, 136 also have attached canted ports (not shown), such as flask necks that can be screw-sealed with caps (e.g., plastic caps), which can be covered by a porous material, such as a hydrophobic microporous (e.g., 0.2 micron pore size) membrane of nylon-coated acrylic polymer (e.g., USP Class 6). These screw-seal ports with caps covered by microporous membrane (not shown) can be similar to the ports attached to the reaction chamber 102 shown in FIG. 2 (e.g., canted ports 208, caps 212, and porous material 212). The porous material allows gas exchange to occur in the containers 134, 136 during an operational run, while preventing microbial contamination of the contents when the containers 134, 136 are covered with top panels (not shown) and the canted ports (not shown) are screw-sealed. In this manner, gas exchange is permitted for the cells in the permeable or semi-permeable collection bag 140, while the environment remains substantially sterile.

Depending upon the type of cell collection bag 140 selected for cell harvest, either a standard syringe-type Luer lock nozzle (not shown) or a large bore needle (not shown) can be attached to the end of the cell collection tubing 120 that runs into the collection container 134. When the cell collection bag 140 is constructed of sterile dialysis tubing or some other permeable or semi-permeable material, as described in the example above, the tubing can be sealed at one end with a sterile clamp, ligature, or other method of closure. The other end of the dialysis tubing cell collection bag 140 can be attached with a sterile clamp, ligature, or other method of closure, over the orifice of a standard syringe-type Luer lock nozzle (not shown) attached to the tubing 120 entering the collection container 134 from the reaction chamber 102. The nozzle can be sealed to the end of the cell collection tubing 120 with epoxy glue or some other connection mechanism. The male connector of the Luer lock nozzle can be press fit connected into the female connector of a large bore needle (not shown). The dialysis tubing collection bag 140 generally lies in the bottom of the collection container. In these embodiments, the cyclic container 136 and the collection container 134 are filled to approximately 12 centimeters (or some other height, as desired) with sterile cell culture medium, and the top panels (not shown) and side screw-cap ports (not shown) of the containers 134, 136 are sealed for the operational run.

When the cell collection bag 12 is a standard intravenous mini-bag or is constructed of some other impermeable material, as described in the example above, it can have a factory-sealed rubber-covered injection port 342, and can also have a second port that is a female connector (not shown) for attachment of a male connector, or "spike" of a connector for intravenous tubing, or some other type of port. A large bore needle (e.g., 18 to 14 gauge; not shown) connected to the collection tubing 120 can be driven into the injection port 342 to connect the tubing 120 to the cell collection bag 140. The large bore needle can be sealed to the end of the cell collection tubing 120 with epoxy glue or some other connection mechanism. In some embodiments, the female connector (not shown) of the second port can be connected ("spiked") to sterile intravenous tubing (not shown), and the tubing can exit from and be sealed into a second opening (not shown) in the lower portion of the container 134 wall. In some embodiments, the intravenous tubing (not shown) is sealed with a stopcock valve (not shown) or other method of closure, and the stopcock valve may be periodically opened in order to drain or flush product cells from the collection bag 140 in the collection container 134 periodically during an operational run. The cell products can be flushed into a second collection bag or other container (not shown) containing fresh culture media and permitting gas exchange. As another alternative, this design can be used to periodically drain cellular wastes from the cell collection bag 140 and circulate in fresh media to the cells in the bag 140. Other similar methods for ensuring that cell products continue to have access to fresh media during the operational run can be used as well. In some embodiments, the evacuated impermeable collection bag 140, with large-bore needle inserted in its injection port 342 generally lies on the bottom of the collection container 134, and both the cyclic container 136 and the collection container 134 are filled to approximately 12 centimeters (or some other desired height) with water for the operational run.

The collection container 134 can include an opening 317 in the lower portion of the container 134 wall. In some embodiments, the opening 317 is approximately 1 or 2 centimeters above its base, and the opening 317 is designed to be slightly wider in diameter than the outside diameter of standard plastic intravenous tubing (e.g., o.d. 0.142 inch). The cell collection tubing 120 that exits from and is sealed into the base of the reaction chamber 102 connects at its other end to the collection container 134 by running through the opening 317 at the base of the container 134. The tubing can also be sealed to the wall of the opening with epoxy glue or some other connection mechanism.

In some embodiments of the invention, the cell collection tubing 120, which connects the reaction chamber 102 to the collection container 134, is fitted with an interposed three-way stopcock valve (not shown). The stopcock valve can periodically close off the tubing from the reaction chamber 102 and open the tubing from the collection container 134 to a third segment of sterile tubing (not shown) in order to drain or flush product cells from the collection bag 140 in the collection container 134 periodically during an operational run. For example, the cells might be periodically released into a second cell collection bag or container (not shown) with fresh media that can also be designed to permit dissolved gas exchange, allowing the cells to have regular access to fresh media and gases. As another alternative, this design can be used to periodically drain cellular wastes from the cell collection bag 140 and circulate in fresh media to the cells in the bag 140. Other similar methods for ensuring that cell products continue to have access to fresh media during the operational run can be used as well. The stopcock valve (not shown) can then be reset so that flow from the reaction chamber 102 to the collection container 134 is re-established, while the third segment of sterile tubing (not shown) is again closed off from the system.

Tubing 338 constructed of a flexible material, such as plastic or rubber, connects the two containers 134, 136 at one or more locations. The cross-sectional area(s) of the flexible tubing 338 connection(s) between the two containers 134, 136 is generally large enough to allow rapid equilibration of fluid levels between the two containers 134, 136. The tubing 338 is also generally flexible and long enough to allow for the two containers 134, 136 to differ in relative elevation. In some embodiments, the hydrodynamic apparatus 104 is designed so that the two containers 134 and 136 vary in relative elevation by approximately 3 centimeters or another suitable amount.

Prior to each operational run, the collection container 134 is sterilized by, for example, ethylene oxide gas, gamma irradiation, or by another sterilization technique, and the entire collection assemblage can be kept in sterile packaging. In some embodiments, both containers 134 and 136 are sterilized prior to each operational run and can be kept in sterile packaging.

As stated above, the cyclic negative pressure differential is composed of two constituent factors in some embodiments. One factor of the cyclic negative pressure differential is a slow constant negative pressure gradient going from atmospheric pressure (zero differential) to a negative pressure value over a time period. The other constituent factor of the cyclic negative pressure differential is a rapidly oscillating pressure differential, which begins cycling from one atmosphere of pressure to a negative pressure value and back to one atmosphere of pressure at an approximately constant cycle rate over a time period. The midpoint of the cycles of the rapidly oscillating pressure differential generally parallels the decrease over time of the slow constant negative pressure gradient.

The cyclical component of the negative pressure differential is created by varying the difference in elevation between the two containers 134, 136. The collection container 134 rests on a block 148 or other type of support to raise the container 134 to approximately the same height as the cyclic container 136. This block 148 rests on a lowering platform 144 that is supported by the lowering apparatus 150. The cyclic container 136 rests on the oscillating platform 146 that is mechanically lowered and raised so that it oscillates at a level approximately even with the collection container 134 (e.g., at atmospheric pressure) to below the level of the collection container 134. For example, the system 100 can be constructed so that the cyclic container 136 oscillates from a position in which it is about at the same height as the collection container 134 to a position in which it is approximately 3 centimeters below the level of the collection container 134. In this example, this oscillation pattern occurs at approximately a constant rate at a frequency of between 10 to 30 cycles per minute (though fewer cycles can be used as suitable). Thus, the oscillation cycle frequency in this example is ⅙ to ½ Hertz and the fluid level oscillates a distance of ±3 cm at about 10 to 30 times per minute or ⅙ to ½ cycles per second. The center point of the oscillating negative pressure differential is initially set at approximately negative 1.5 centimeters of water (i.e. ranging from 0 to −3 cm.), and this center point decreases slowly in parallel with the rate of decrease of the first element, the constant negative pressure gradient.

The oscillation apparatus 152 that lowers and raises the oscillation platform 146 can be constructed in various manners. For example, the oscillation apparatus 146 can be a device that is driven by mechanical means, by hydraulic means, by gas pressure activated methods, or by a combination of these methods. The oscillation apparatus 152 can include a motor for automatically oscillating the platform 146 up and down, a gear and/or pulley assembly for oscillation, an inflatable support device that can be inflated and deflated to produce oscillations, or any other suitable type of oscillation mechanism. If the hydrodynamic apparatus 104 is kept in an incubator, a substantially waterproof device for lowering and for the creating the oscillations may be necessary. The apparatus 152 could also be a cantilever that is slowly closed by a motor-driven screw mechanism, causing the diagonal struts of the cantilever to close during each oscillation. In another embodiment, a pump or hydraulic system can be used to generate the cyclic negative pressure differential. Various pumps and other types of systems are described in more detail below.

In some embodiments, the hydrodynamic apparatus 104 further includes or rests upon an agitator or other type of device that provides gentle movement of the apparatus 104 to maintain suspension of the cells in the collection bag 140. In other embodiments, just the cyclic component 130 rests on an agitator or some other agitation means (or block 148 can be designed to provide gentle agitation for the cells) that is used to provide gentle motion to the cell collection bag 140 to maintain suspension of the cells.

In some embodiments, the hydrodynamic apparatus 104 and/or reaction chamber 102 can be connected to a computer, a sensor, or other device to allow external control and adjustment of the number of oscillations per minute, the distance of each oscillation, the cyclic negative pressure differential created, etc. The apparatus 104 can alternatively be set to vary in oscillation size and frequency throughout an operational run. The computer, sensor or other device might also control the oscillation cycle to ensure gentle action to maintain suspension of the cells in the collection bag 140. Additionally, the device might also provide data to the user regarding the internal environment in the bioreactor (e.g., temperature, pH, $O_2$ or $CO_2$ content, redox potential, contaminants, etc.), the number of cells collected over time, characteristics of the cells, etc., or may be able to sense any resistance by the fluid, the fluid level, the fluid movement and/or oscillations, the pressure inside the bioreactor, etc. Local sensors may also be positioned in useful locations in the bioreactor system (e.g., near the cell collection bag 140) for sensing the local environment (e.g., environment in the cell collection bag 140 or characteristics of collected cells).

To create the slow constant negative pressure gradient between the reaction chamber 102 and the cell collection bag 140 in the collection container 134, the two containers 134, 136 and their support platforms 146, 148 are all situated on a lowering platform 144 that is slowly lowered relative to the reaction chamber 102 (e.g., at a rate of 1.5 mm/hr). Thus, the hydrodynamic apparatus 104 decreases in height relative to the reaction chamber 102 during an operational run. In some embodiments, the hydrodynamic apparatus 104 is lowered at a rate of approximately 3 to 6 centimeters (or another suitable amount) over 24 hours (or another suitable time period). Thus, in these embodiments, the oscillating apparatus 152 lowers and raises the cyclic container 136 relative to the collection container 136 while the lowering apparatus 150 lowers the platform 144 and both of the containers 134, 136 slowly and constantly over time. In some embodiments, the overall pressure drop over 24 hours due to this slow constant negative pressure gradient is about 4 to 6 cm starting from atmospheric pressure. Thus, the relative hydrostatic pressure in the cell collection bag 140 will be gradually reduced by 4 to 6 cm of water compared to the hydrostatic pressure in the reaction chamber. In other embodiments, the overall pressure drop is about 3 to 6 cm starting from atmospheric pressure.

The apparatus 150 that lowers the platform 144 can be constructed similarly to and can operate similarly to the oscillation apparatus 152, examples of which were previously described. In some embodiments, the hydrodynamic apparatus 104 is contained within an incubation chamber in which the pressure is controlled to assist in the creation of the cyclic negative pressure differential as described above. In some embodiments, the containers 134, 136 are covered (and are thus not open to the atmosphere) to assist in the creation of the cyclic negative pressure differential.

In another embodiment of the present invention, the hydrodynamic apparatus 104 and the reaction chamber 102 are not separate components, but instead are included within the same component within the bioreactor system 100. In other embodiments, the hydrodynamic apparatus 104 and reaction chamber 102 are separate components, but the hydrodynamic apparatus 104 includes only one container 134 (e.g., a beaker, a flask, etc.), and this one container 134 is used for collection of cells in a collection bag 140 and also for creation of a cyclic negative pressure differential. For example, the container 134 in this embodiment might include a pump or other hydraulic device (not shown) that replaces the cyclic component 132 and is attached to the container 134 for pumping water or culture medium into and out of the container to create the oscillating fluid level. The container 134 can be lowered relative to the reaction chamber 102 over time to create the negative pressure differential, or the pump can be designed to pull water or culture medium out of the container 134 over time to create the negative pressure differential. The pump can also be designed to have a gentle oscillation cycle to maintain suspension of the cells in the collection bag 140. For example, the pump might include a relief valve for release of fluid if necessary, or the pump may be connected to a sensor for sensing any resistance by the fluid and controlling the amount of fluid moved by the pump.

In another embodiment, the pump or hydraulic system can be positioned at the top of the cyclic container 136 to press down on the fluid beneath. The pump can be oscillated up and down to create the cyclic component of the cyclic negative pressure differential by pressing down on the water or culture medium in the cyclic container 136. In other embodiments of the present invention, the hydrodynamic apparatus 104 can include various other pump designs for generating a cyclic negative pressure differential in the bioreactor system 100. For example, the containers 134 and 136 of the hydrodynamic apparatus 104 can be closed components and an air pump or some other mechanism for transferring air can be used to pull air out of either of the two closed components to decrease the pressure on the fluid inside the component and adjust the fluid level. The same air pump or another pump can be used to push air into either of the two closed components to increase the pressure on the fluid inside the component and again adjust the fluid level. In this manner, the fluid levels and pressures inside the components of the can oscillate. Over time, the components can be lowered relative to the reaction chamber to create an added negative pressure differential, or the pump can be set to pull additional air out of the container over time to create the added negative pressure differential. Again, sensors or relief valves can be used if needed to control the cyclic negative pressure differential created and to ensure gentle action to maintain suspension of the cells in the collection bag 140.

Methods of Tissue Cultivation

The methods of tissue cultivation according to an embodiment of the present invention are described herein. In the embodiments described below, the tissue cultivation method is illustrated in reference to engineering of bone marrow tissue to produce and cultivate blood cells. However, the methods of the present invention are not limited to engineering of bone marrow tissue to produce and cultivate blood cells, and can also be used in a number of different applications. For example, the bioreactor system 100 can be used in the generation of recombinant proteins (e.g., growth hormone), generation of tumor cells, generation of liver cells, or other types of cells. In addition, the cells, proteins, etc. generated by this bioreactor system 100 can be human cells, animal cells, plant cells, bacterial cells, or cells from any multicellular or unicellular organism. Thus, the methods described below are only one example of the use of the bioreactor system 100. The bioreactor system 100 can be used in a number of different manners and can be used with different tissue engineering and/or cell collection methods. Additionally, the steps of the below-described methods can be modified or removed as appropriate. The example is offered for illustrative purposes only, and is not intended to limit the scope of the present invention in any way. Efforts have been made to ensure accuracy with respect to numbers used (e.g., amounts, temperatures, etc.), but some experimental error and deviation should, of course, be allowed for.

The methods of tissue cultivation according to an embodiment of the present invention include five components. The four biological components of the ex vivo in vitro marrow cell and tissue cultivation system for production and cultivation of blood cells include the harvest and preparation of 1) marrow stromovascular extracellular matrix; 2) stromal spindle cells; 3) endothelial cells; and 4) hematopoietic progenitor cells. The fifth component of the methods of tissue cultivation includes the recombination of these matrical and cellular components for in vitro tissue cultivation, and description of the cell culture medium and additives and the cell culture environmental conditions.

Harvest and Preparation of marrow stromovascular extracellular matrix

In some embodiments, bone marrow extracellular matrix and cells are harvested from the femora and tibiae of euthanized Fisher 344 rats (e.g., from CHARLES RIVER LABORATORIES™) in the following manner. Either young adult male or female rats are obtained as research animal subjects, in some embodiments. However, sex selection may be used to ensure genetic markers unique to the Y chromosome be available for definition of cell lineages in other embodiments. The research animal subject is given an intraperitoneal injection of pentobarbital at the dosage of 100 mg/Kg, and allowed to proceed to comatose state. The abdomen and lower extremities are shaved and prepped with Betadine, then blotted with sterile gauze coated with 95% ethanol. Rubber band restraints are applied to the animal's wrists and ankles and the loose ends are tacked down with the animal supine. Immediately upon the expiration of the animal, as determined by cessation of heartbeat, the abdomen is opened by a midline longitudinal incision carried down in layers to expose and open the peritoneal cavity. The small intestine is retracted craniad to expose the underlying aorta and vena cava. Above its bifurcation, a segment of aorta is exposed by blunt dissection and is cannulated with 18 gauge sterile tubing attached to an injection syringe containing 90% Ringer's solution and 10% glycerol cryoprotectant. The vena cava is then incised and the lower extremities are perfused until relative clearing of the outflow from the vena cava.

The cadaver is then re-prepped with Betadine and EtOH, and the lower extremities are draped for sterile necropsy. By dissection, the leg and thigh are opened and the femora and tibiae are placed in a filter-sterilized (0.2 µm) 90/10% solution of Ringer's/glycerol. Metaphyseal segments of 3 to 5 mm are frozen to −20° C. on and in Optimal Cutting Temperature, or O.C.T. (e.g., from SAKURA®), and are coronally frozen and sectioned at intervals of 1 to 2 mm on a sledge microtome. The sections are placed in a cell lysis solution of phosphate-buffered saline containing 20 mM $NH_4OH$ and 0.5% (v/v) TRITON® X-100. The incubation for cell lysis is at 37° C. is generally from about 2 to 10 minutes. Sample coronal metaphyseal sections can be evaluated periodically by light microscopy to evaluate residual cellularity and histoarchitecture. In some embodiments, the methods may include collagenase (e.g., from SIGMA™) in the lysis solution. Use of frozen sectioning with cryoprotectant is most effective with enhanced cell lysis due to the freeze-thaw cycle. However, the methods may also include control metaphyseal coronal sections made with fine-tooth wire saw. The methods are designed to best preserve the biochemistry of the marrow stroma and the mineralization of the cancellous bony architecture. The acellular marrow tissue sections are used as in vitro substrates for stromal and endothelial cell cultivation, or are stored until such usage, at 4° C. on and under PBS moistened gauze, or stored frozen (e.g., at −20° C.).

Harvest and Preparation of Stromal Spindle Cells

The harvest of marrow stromal spindle cells, endothelial cells, and hematopoietic progenitor cells all commence similarly. Fisher 344 rat animal research subjects are given euthanasia by intraperitoneal injection of pentobarbital 100 mg/Kg. After expiration, the lower extremities are shaved, prepped with Betadine and EtOH, and draped for necropsy dissection and harvest of the femora and tibiae, which are placed in sterile MEM without serum. The articular ends of the bones are removed just subjacent to the subchondral plate, and the contents of the metaphyseal/diaphyseal bone are flushed into a sterile test tube with a 18 to 20 gauge needle/syringes containing sterile BJGb medium (e.g., from GIBCO INDUSTRIES, INC.™) with 18% Fetal Bovine Serum or FBS (e.g., from GIBCO™) and 0.05% Heparin.

Following passage of the crude marrow cell suspension three times through 19 to 21 gauge needles, the marrow/medium suspension is placed in a centrifuge tube (e.g., from CORNING, INC.™) on top of a discontinuous density gradient, recently manufactured with 66% FICOLL-PAQUE™ over undiluted FICOLL-PAQUE™. After 30 minutes centrifugation at 300 G, the light density cells are collected, recentrifuged briefly, and re-suspended in cell culture medium. Because stromal spindle cells are the most adherent and most proliferative of a mixed dispersion of primary bone marrow cells, stable cell lines are easily established by primary plating in cell culture flasks (e.g., BD FALCON™ from BECTON-DICKINSON BIOSCIENCES™) with BJGb medium and 18% FBS, glutamine, antibiotics and antimycotic in a 37° C., 5% $CO_2$ incubator. After approaching confluency, stromal cell lines are maintained by passage with Trypsin-EDTA dispersion, or aliquots may be frozen at −72° C. for subsequent retrieval.

Harvest and Preparation of Endothelial Cells

By electron microscopy, marrow endothelial cells consist of at least three identifiable populations, sinusoidal, capillary, and arteriolar. For that reason, at least two antibodies are to be used for immunomagnetic affinity selection and establishment of marrow endothelial cell lines: as primary antibodies, a mouse anti-rat PECAM (CD31) (e.g., from B-D BIOSCIENCES™) or a mouse anti-rat RECA-1 pan-endothelial (e.g., from SEROTEC™) or anti-rat P-selectin (CD62) (e.g., SEROTEC™) or other commercially available antibody, as suitable. Super-paramagnetic microbeads for magnetic activated cell storing (e.g., MACS® MICROBEADS from MILTENYI BIOTEC®), which are conjugated to a second antibody, such as anti-mouse immunoglobulin, are used for the immunomagnetic affinity selection of marrow endothelial cells. The harvest of endothelial cells for propagation starts with the same harvest of femora and tibiae in sterile MEM without serum. The marrow contents are similarly flushed into a sterile test tube with 18 to 20 gauge needle/syringes containing sterile MEM medium without serum but with 0.05% Heparin, dispersed through 19 to 21 gauge needles, and separated by similar FICOLL-PAQUE® isopycnic centrifugation. The light density cells are collected, washed, then incubated with anti-endothelial cell primary antibody, followed by MACS® MICROBEAD (or other type of bead) conjugated secondary antibody, and immunomagnetic selection is done with a MILTENYI MINIMACS® permanent magnet. The selected cells are then cultivated with MEM with FBS, under similar culture conditions, showing typical tiled appearance by phase microscopy.

Harvest and Preparation of Hematopoietic Progenitor Cells

The harvest of marrow hematopoietic stem or progenitor cells starts with the same harvest of femora and tibiae in sterile MEM without serum. The marrow contents are similarly flushed from the bone and dispersed by gentle mechanical dispersion through needles. The light density cells are collected, washed, and incubated with either or both mouse anti-rat thy-1 (e.g., from SEROTEC™) and mouse anti-human CD34, cross-reacting with rat CD34 (e.g., from Santa Cruz) primary antibodies. Super-paramagnetic MACS® MICROBEADS conjugated to an anti-mouse immunoglobulin second antibody can be used for the immunomagnetic affinity selection of marrow hematopoietic stem or progenitor cells. Hematopoietic stem or progenitor cells are fastidious in their culture requirements, requiring hematopoietic growth factors and/or a "feeder" layer of marrow stromal cells. For that reason, they can be primary plated to the bioreactor substrate of previously prepared marrow stromovascular matrix, which is re-populated 24 hours prior with defined populations of marrow stromal spindle cells and marrow-derived endothelial cells.

Recombination of Matrical and Cellular Components

The methods for tissue engineering an ex vivo in vitro marrow cell and tissue cultivation system are designed to produce mature blood cells, erythrocytes, leucocytes, and/or platelets. However, it is possible that in some instances, phenotypically mature blood cells will be nonadherent, will be discharged into the cell culture medium, and will remain viable in suspension. These properties should allow for continuous harvest and collection from the marrow cell and tissue cultivation system without interference to continuing hematopoietic cell growth, maturation, and liberation. The acellular marrow tissue sections prepared are plated with aliquots of the prepared marrow stromal cells and the prepared endothelial cells and allowed to incubate overnight in MEM with FBS under standard cell culture conditions. The next day, hematopoietic stem or progenitor cells are harvested, selected, and plated onto the repopulated marrow cell tissue sections. The repopulated marrow tissue with hematopoietic stem or progenitor cells are cultivated in the closed bioreactor system 100 containing MEM with HS and hematopoietic growth factors, including erythropoietin, antibiotics and antimycotic. In some embodiments, the repopulated marrow tissue with hematopoietic stem or progenitor cells are cultivated in the closed bioreactor system 100 containing other formulations of medium (e.g., 199) or formulations of medium containing other serum (e.g., FBS or formulations of defined medium without serum (e.g., serum-free medium). The bioreactor 100 is maintained in the 37° C., 5% $CO_2$ incubator, and has gas exchange via a hydrophobic 0.2 micron membrane. Blood cellular products discharged into the medium are continuously collected by a fluidic mechanism. Analysis of the cells is conducted using Wright stain microscopy, and analysis of the marrow cell and tissue cultivation system is conducted using light microscopy or flow cytometry.

Operation of the Bioreactor System

Once the engineered hematopoietic marrow tissue is prepared, the diffusion chambers 114 are loaded with engineered hematopoietic tissue, as stated above. For example, one porous covering 202 can be loaded with the tissue and attached to the outer ring 244, and another porous covering 202 can be sealed to the other side of the outer ring 244 to trap the tissue inside the porous diffusion chamber 114. In some embodiments, the loaded and sealed diffusion chamber 114 assemblage is placed, tubing side down, into the reaction chamber 102, and the large bore needle is driven into the rubber-covered injection port 218 on the tubing exiting the reaction chamber 102 base.

Cell culture medium can be added to the reaction chamber 102 to a certain height (e.g., 12 centimeters). The top panel 102 and side screw cap canted ports 208 of the reaction chamber 102 are sealed to ready the bioreactor 100 for an operational run. In some embodiments, the reaction chamber 102 contents are stirred during an operational run. For example, a sterile Teflon-coated magnetic stir-bar, previously placed on the floor of the reaction chamber 102, can be made to spin in the bottom of the reaction chamber 102 during operational runs so that gradients of dissolved gases, temperature, or pH cannot develop in the cell culture medium 222.

In some embodiments, during an operational run, the relative hydrostatic pressure in the cell collection bag 140 will be gradually reduced by approximately 3 to 6 centimeters of water (illustrated by arrow 204 in FIGS. 2 and 6) compared to the hydrostatic pressure in the reaction chamber 102. The pressure differential causes the cell culture medium 222 in the reaction chamber 102 to filter through the porous coverings 202 into the diffusion chambers 114 to perfuse the engineered hematopoietic tissue inside the chambers 114. The same pressure differential causes blood cells shed by the engineered hematopoietic tissue to move down into and along the tubing 216 at the bottom of the diffusion chambers 114 and out through the cell collection tubing 120 for harvest in the collection bag 140 in the hydrodynamic apparatus 104. For the diffusion chambers 114 to remain below the surface of the cell culture medium 222 in the reaction chamber 102 throughout the entire course of each operational run, the cell culture medium 222 can be added to the reaction chamber 102 to a height of at least 3 to 6 centimeters above the diffusion chambers 114 at the beginning of each operational run.

The negative pressure differential created between the diffusion chambers 114 and the blood cell collection bag 140 by the hydrodynamic apparatus 102 causes a net flow down the tubing 120 into the bag 140 for harvest of the blood cells being produced by the engineered hematopoietic tissue in the diffusion chambers 114. The net flow rate down the tubing 120 and into the blood cell collection bag 140 is approximately 1 or 2 milliliters per hour, in some embodiments of the present invention. However, this net flow rate can be varied if the cyclic negative pressure differential is modified. In some embodiments, the total negative hydrostatic pressure differential (in centimeters of water) is less than the difference in heights between the height of the cell culture medium 222 in the reaction chamber 102 and the height of the water in the cyclic container 136. This is because there is impedance to flow and resistance to pressure by the porous coverings 202 that the cell culture medium 222 must traverse to enter the diffusion chambers 114, as well as the resistance and impedance of the tubing 216, 120 and the collection bag 140. In some embodiments of the present invention, the bioreactor system 100 includes a reservoir mechanism (not shown) for adding additional cell culture medium 222 to the reaction chamber 102 during operation. In some embodiments, operational runs may be continued for multiple days by the simultaneous addition of cell culture medium to the reaction chamber 102 up to the original starting fluid height and the concomitant repositioning of the hydrodynamic apparatus so that both the collection container 134 and the cyclic container 136 are also repositioned at their original starting heights. In some embodiments, the bioreactor system 100 includes sealed electrical ports (not shown) for probes to continuously monitor pH, dissolved oxygen, redox potential, and other characteristics of the cell culture medium of the reaction chamber during operation (or before or after operation).

Referring to FIGS. 3, 4, 5, and 6, there is shown the operation of the hydrodynamic apparatus 104 according to an embodiment of the present invention. FIG. 3 illustrates the hydrodynamic apparatus 104 at the starting position, with the fluid levels in each of the containers 134, 136 being at about the same height. The oscillating apparatus 152 is in the raised position to bring the cyclic container 136 to about the same height as the collection container 134. In addition, the lowering apparatus 150 is in the raised position so that the platform 144 is at the highest position before the lowering process begins.

Figure 4:
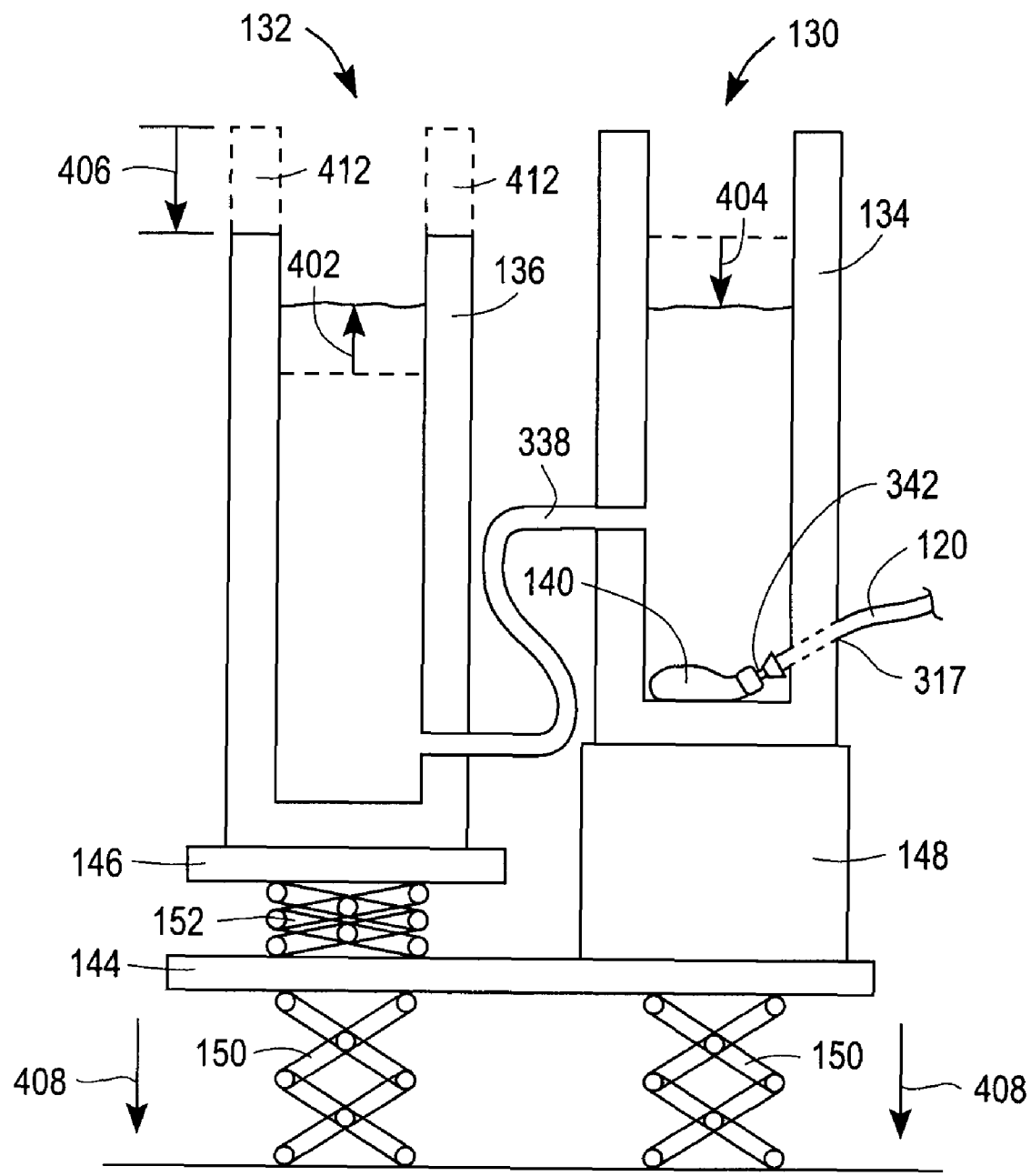
FIG. 4 is a diagram of the components of the hydrodynamic apparatus during the cell collection time period, illustrating a downward oscillation.

FIG. 4 illustrates a downward oscillation of the cyclic component 132 according to an embodiment of the present invention. In this Figure, the oscillating apparatus 152 is in a lowered position, and the platform 146 is in its lowered position, thereby lowering the cyclic container 136 relative to the collection container 134, as shown by arrow 406. As illustrated in FIG. 4, the dotted lines labeled 412 show the original position of the cyclic container 136, as it was positioned in FIG. 3. In some embodiments, the cyclic container 136 has been lowered by approximately 3 centimeters relative to the collection container 134. In addition, the fluid level in the cyclic container 136 has risen from its original position in FIG. 3 (shown by the dotted line) to the new position as illustrated by arrow 402. The fluid level in the collection container 134 has been lowered from its original position in FIG. 3 (shown by the dotted line) to the new position as illustrated by arrow 404. Thus, the fluid levels of each of the containers 134, 136 have changed upon oscillation to equilibrate and once again be approximately at the same height. FIG. 4 also illustrates the negative pressure element since platform 144 is being lowered constantly and slowly as controlled by apparatus 150. The platform 144 is moving in the direction illustrated by arrow 408.

Figure 5:
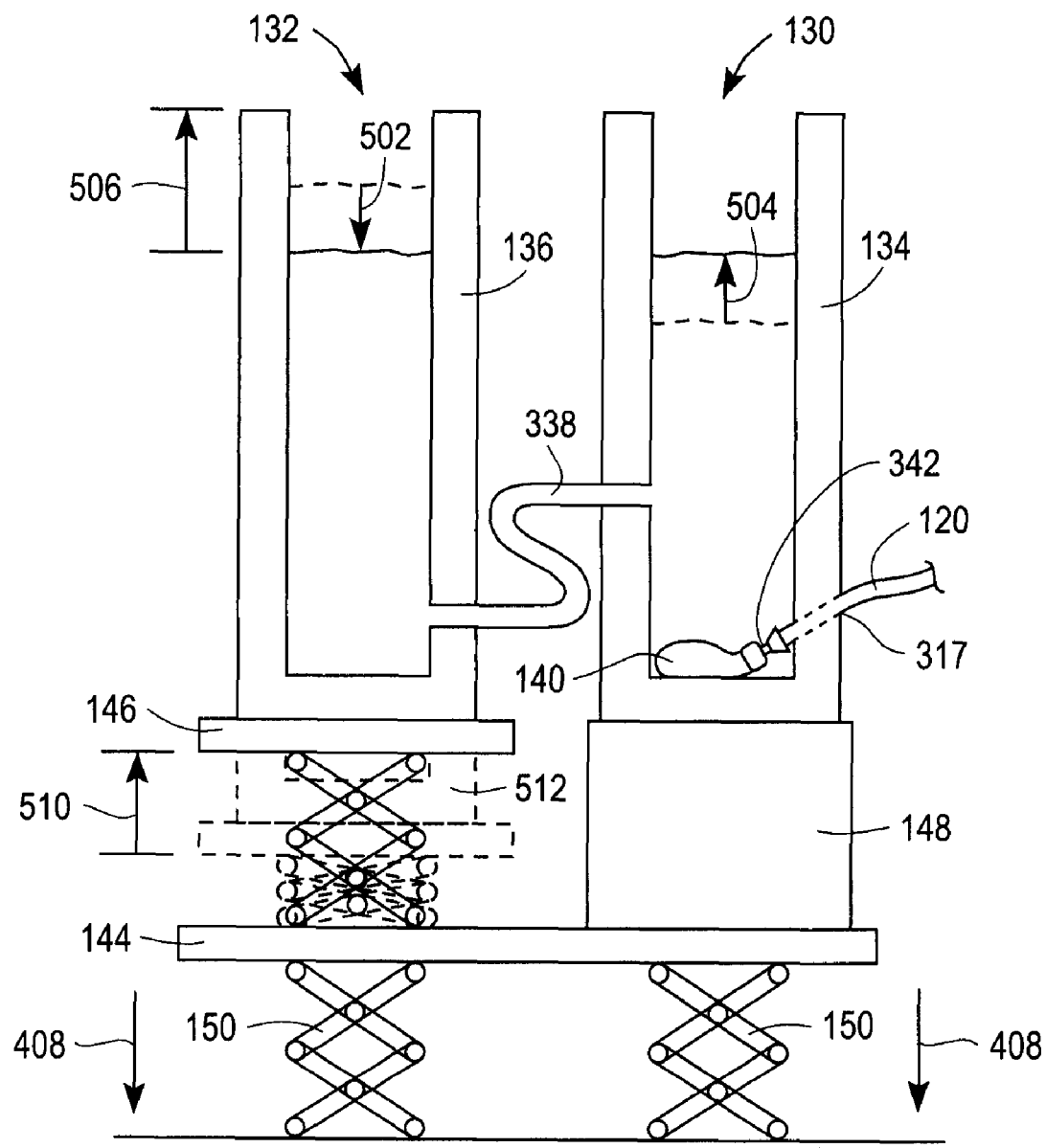
FIG. 5 is a diagram of the components of the hydrodynamic apparatus during the cell collection time period, illustrating an upward oscillation.

FIG. 5 illustrates an upward oscillation of the cyclic component 132 according to an embodiment of the present invention. In this Figure, the oscillating apparatus 152 is in a raised position, and the platform 146 is in its raised position, thereby raising the cyclic container 136 relative to the collection container 134, as shown by arrow 506. As illustrated in FIG. 5, the dotted lines labeled 512 show the original position of the cyclic container 136, as it was positioned in FIG. 3, and arrow 510 shows the direction in which the container 136 moved. In some embodiments, the cyclic container 136 has been raised by approximately 3 centimeters relative to the collection container 136. In addition, the fluid level in the cyclic container 136 has been lowered from its original position in FIG. 3 (shown by the dotted line) to the new position as illustrated by arrow 502. The fluid level in the collection container 134 has risen from its original position in FIG. 3 (shown by the dotted line) to the new position as illustrated by arrow 504. Thus, the fluid levels of each of the containers 134, 136 have changed upon oscillation to equilibrate and once again be approximately at the same height. The fluid travels within tubing 338 connecting the containers 134, 136 to create the oscillations felt by the cell collection bag 140. FIG. 5 also illustrates the negative pressure element since platform 144 is being lowered as shown by arrow 408 constantly and slowly as controlled by apparatus 150.

Figure 6:
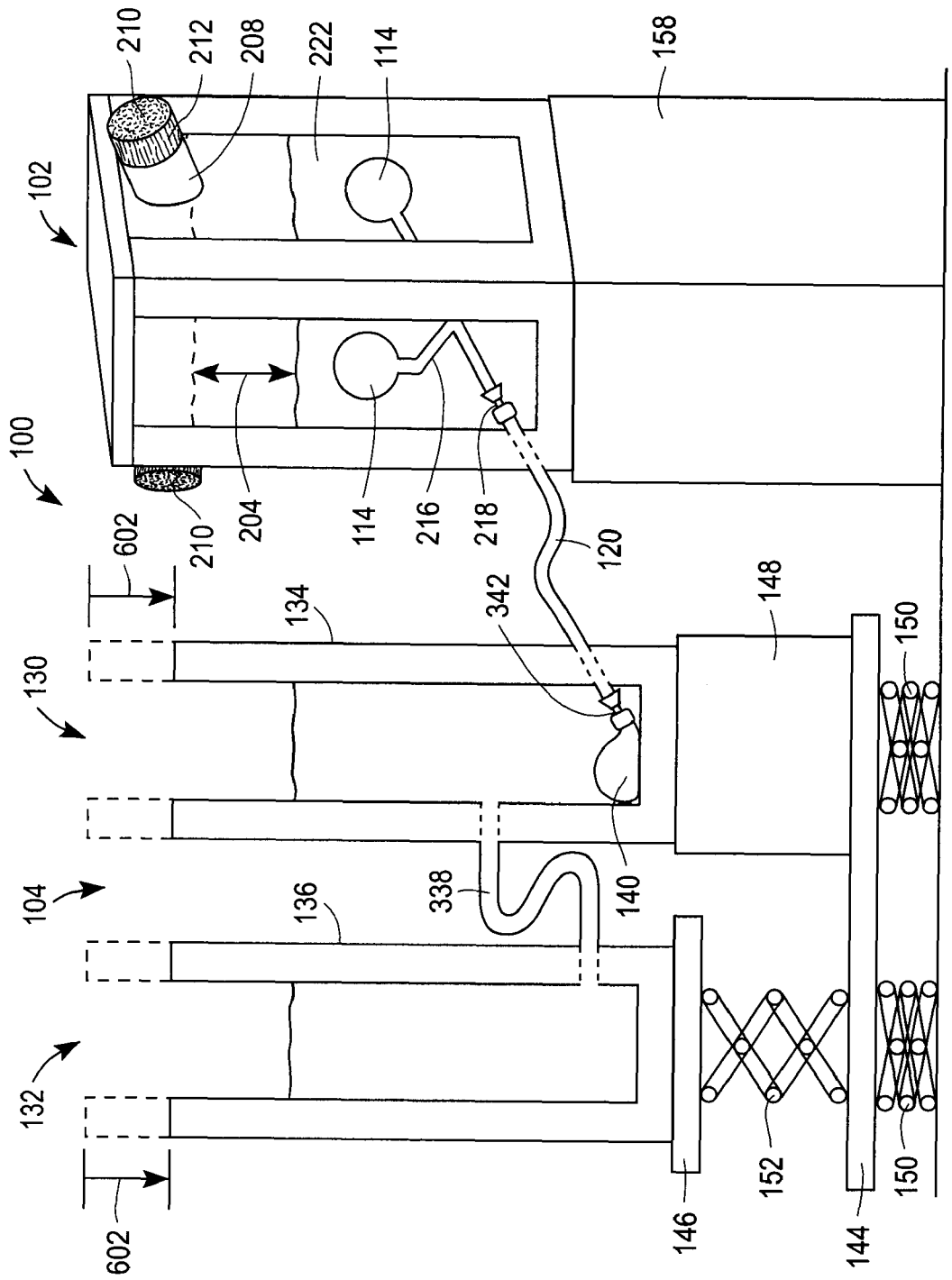
FIG. 6 is a diagram of the bioreactor system at the end of the cell collection time period.

FIG. 6 illustrates the ending position of the bioreactor system 100 according to an embodiment of the present invention. Apparatus 150 has lowered platform 144 to its end position, thereby lowering both containers 134 and 136. In some embodiments, the containers 134, 136 are lowered by approximately 3 to 6 centimeters in the direction illustrated by arrow 602. In addition, the fluid level in the reaction chamber 103 has lowered from its original position (shown by dotted lines) in the direction illustrated by arrow 204. In some embodiments, the reaction chamber 102 fluid level drops by approximately 3 to 6 centimeters in height. In some embodiments, after a time period (e.g., approximately 24 hours) the cell culture medium fluid height in the reaction chamber 102 can be restored to its original position (shown by dotted lines) from a reservoir (not shown), while at the same time the hydrodynamic apparatus is repositioned so that both the collection container 134 and the cyclic container 136 are restored to their original starting heights, allowing the operational run to continue for an additional time period (e.g., approximately 24 hours). In some embodiments, the intermittent but simultaneous restoration of medium fluid height in the reaction chamber 102 and repositioning of both the collection container 134 and cyclic container 136 to original starting heights, can allow an operational run to continue multiple days or weeks. In addition, FIG. 6 illustrates a full collection bag 140 indicating that the reaction has occurred and the harvested cells traveled from the diffusion chambers 114 to the cell collection bag 140.

Figure 7A:
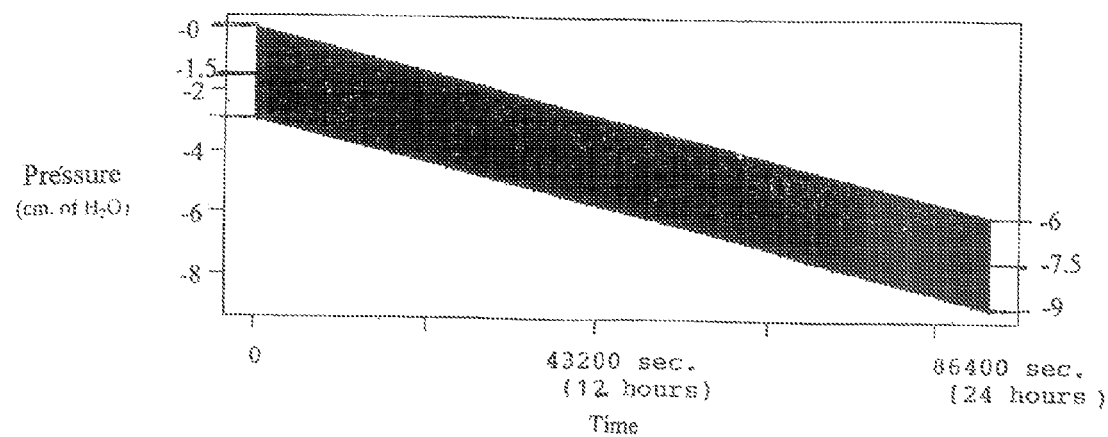
FIG. 7A is a graph illustrating the cyclic negative pressure created in the bioreactor system over a 24-hour time period.
Figure 7B:
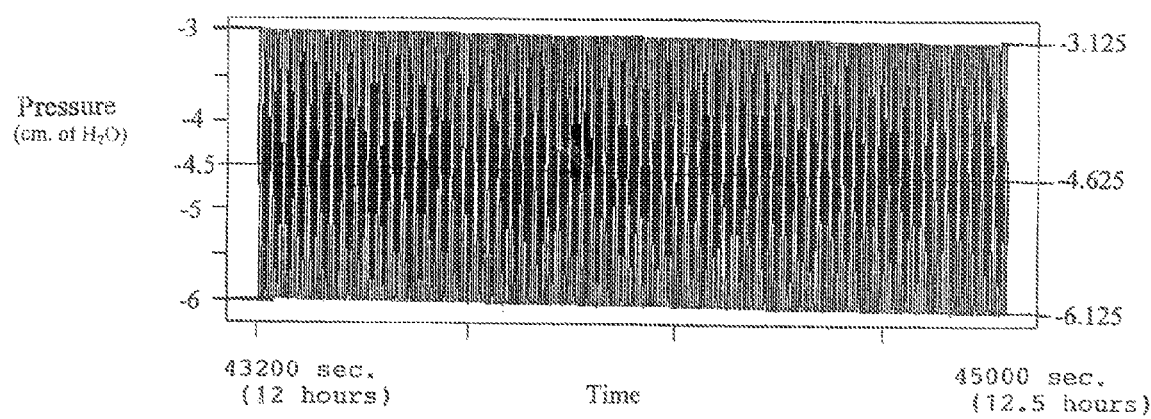
FIG. 7B is a graph illustrating the cyclic negative pressure created in the bioreactor system over a 30-minute time period.
Figure 7C:
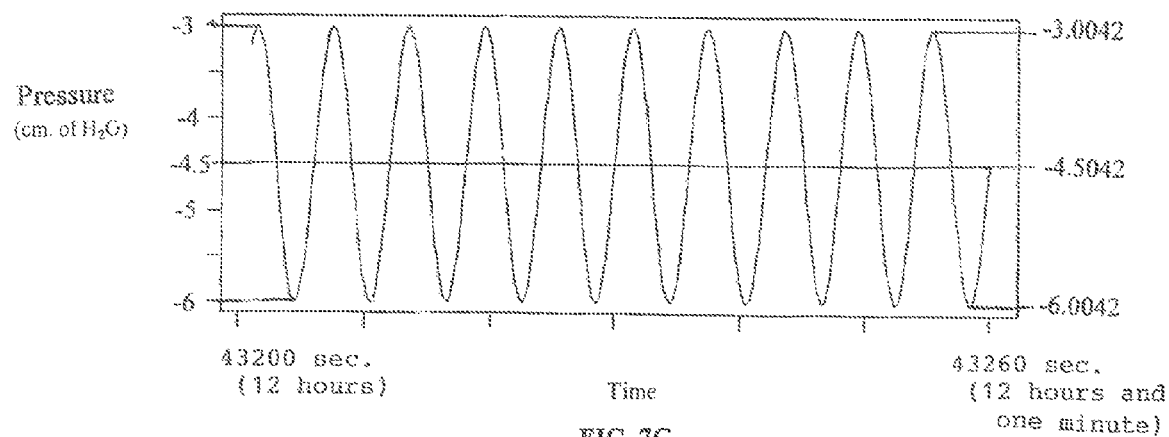
FIG. 7C is a graph illustrating the cyclic negative pressure created in the bioreactor system over a 1-minute time period.

Referring now to FIGS. 7A, 7B, and 7C, there are shown graphical representations of the cyclic negative pressure differential according to an embodiment of the present invention. The negative pressure in centimeters of water is depicted on the y-axis and the time period of the operational run is depicted on the x-axis. FIG. 7A depicts 10 oscillations per minute starting at between 0 (atmospheric pressure) to −3 centimeters of water in the cyclic container 136 over 24 hours. The center point of the oscillating negative pressure differential is initially set a −1.5 centimeters of water (i.e., ranging from 0 to −3 centimeters) and this center point decreases slowly in parallel with the rate of decrease of the constant negative pressure gradient. Thus, the center point of the total overall change in negative pressure at half way through one day (24 hours) of an operational run of the bioreactor (12 hours) is approximately −4.5 centimeters of water (i.e., ranging from −3 to −6 centimeters). At the end of one day of the operational run (24 hours or 86,400 seconds) the center point is at approximately −7.5 centimeters of water (i.e., ranging from −6 to −9 centimeters), as depicted in FIG. 7A on the y-axis on the right-hand side of the graph. Thus, the graph also shows the total overall change in negative pressure in centimeters of water in the reaction chamber as the containers 134 and 136 are both lowered. The high frequency of oscillations of the fluid level in the cyclic container 136 are only visible in FIG. 7A as a dark band over the entire 24-hour time period (86,400 seconds) of the 24-hour operational run, since ten oscillations are occurring per minute in this example. While FIG. 7A does not clearly show each oscillation that is occurring over the 24-hour time period, FIG. 7A does show the overall fluid level height decrease in the reaction chamber 102 (and overall decrease of hydrostatic pressure felt by the collection bag 140) by approximately 6 cm.

FIGS. 7 B and 7 C depict portions of the graph shown in FIG. 7A. FIG. 7B illustrates a 30-minute segment of graph 7A at approximately halfway through one day (24 hours) of an operational run of the bioreactor. Thus, the graph illustrates the negative pressure in the bioreactor system 100 from 12 hours (43,200 seconds) to 12 hours and 30 minutes (43,500 seconds). In this Figure, the oscillations are more clearly visible than they were in FIG. 7A, showing 10 oscillations per minute in that 30-minute period. In FIG. 7B, the negative pressure is oscillating between −3 centimeters of water and −6 centimeters of water, with a center point at −4.5 centimeters of water. The y-axis on the right-hand side of the graph illustrates the drop in overall pressure over the 30-minute increment (i.e., the center point drops from 4.5 centimeters to −4.625 centimeters of water over 30 minutes, and the negative pressure is oscillating between −3.125 and −6.125 centimeters of water at the end of the 30-minute period).

FIG. 7C illustrates a 1-minute segment of graph 7A at approximately halfway through one day (24 hours) of an operational run of the bioreactor. Thus, the graph illustrates the negative pressure in the bioreactor system 100 from 12 hours (43,200 seconds) to 12 hours and 1 minute (43,260 seconds). In this Figure, the oscillations are even more clearly visible than they were in FIGS. 7A and 7B, showing 10 oscillations in that 1-minute period. In FIG. 7C, the negative pressure is oscillating between −3 centimeters of water and −6 centimeters of water, with a center point at −4.5 centimeters of water. The y-axis on the right-hand side of the graph again illustrates the drop in overall pressure, which is a small drop over this 1-minute segment (i.e., the center point drops from −4.5 centimeters to −4.5042 centimeters of water over 30 minutes, and the negative pressure is oscillating between −3.0042 and −6.0042 centimeters of water at the end of the 1-minute period).

In summary, the negative pressure action of the hydrodynamic apparatus 104, including the superimposed cyclic oscillations illustrated in FIGS. 7A, B, and C, imitates the pressure differential between the tissue interstitial or extracellular pressure (tissue turgor) and the intravenous or venular intravascular pressure. This hydrodynamic apparatus 104 reproduces a cyclic negative pressure differential between the engineered hematopoietic tissue in the diffusion chambers 114 in the reaction chamber 102 and the blood cell harvest and collection bag 140 of the hydrodynamic apparatus 104.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Cabrita, G., Ferreira, B., da Silva, C., Goncalves, R., Almeida-Forada, G., Cabral, J. 2003. Hematopoietic Stem Cells: from the bone to the bioreactor. *Trends Biotechnol.* 21(5): 233-240.
2. Januszewski, M., Dabrowski, Z., Adamus, M., Niedzwiedzki, T. 2003. Three-dimensional Model of Bone Marrow Stromal Cell Culture. *Biomed. Mater. Eng.* 13(1): 1-9.
3. Mantalaris, A., Keng, P., Bourne, P., Chang, A., Wu, J. 1998. Engineering a Human Bone Marrow Model: a case study on ex vivo erythropoiesis. *Biotechnol. Prog.* 14(1): 126-133.
4. Naughton, B., Tjota, A., Sibanda, B., Naughton, G. 1991. Hematopoiesis on Suspended Nylon Screen-Stomal Cell Microenvironments. *J. Biomech. Eng.* 113(2): 171-177.
5. Nielsen, L. 1999. Bioreactors for Hematopoietic Cell Culture. *Annu. Rev. Biomed. Eng.* 1: 129-152.
6. Noll, T., Jelinek, N., Schmid, S., Biselli, M., Wandrey, C. 2002. Cultivation of Hematopoietic Stem and Progenitor Cells: biochemical engineering aspects. *Adv. Biochem. Eng. Biotechnol.* 74: 111-128.
7. Rice, H., Emani, V., Skarsgard, E., Knazek, R., Zanjani, E., Flake, A., Harrison, M. 1994. Human Fetal Liver Hematopoietic Cell Expansion with a Novel Bioreactor System. *Transplant Proc.* 26(6):3338-3339.
8. Trentin, J. 1970. Influence of the Haematopoietic Organ Stromal 'Haemopoietic Microenvironment' on Stem Cell Differentiation. *Regulation of Hematopoiesis.* Volume 1, p. 161-186, Gordon, A. S. (Editor), Meredith (publ.).

What is claimed is:

1. A method for growing cells in a bioreactor including a reaction chamber and a collection enclosure, the method comprising:
   harvesting and preparing cells and a tissue section to be combined for cultivation;
   combining the cells and the tissue section in a culture medium in the reaction chamber to cultivate tissue;
   maintaining the tissue under conditions that permit production of cell products;
   applying cyclic negative pressure to the culture over a period of time that re-creates the pressure differential between tissue interstitial pressure and outflow capillary and venular pressure in mammals; and
   collecting the cell products discharged in a collection enclosure.

2. The method of claim 1, wherein applying cyclic negative pressure over a period of time further comprises applying cyclic negative pressure over each 24-hour time period of an operational run of the bioreactor.

3. The method of claim 1, further comprising decreasing the culture medium level from 3 to 6 centimeters of fluid over each 24-hour time period of an operational run.

4. The method of claim 1, wherein applying cyclic negative pressure comprises creating a cyclic negative pressure differential between the collection enclosure and the reaction chamber by oscillating fluid surrounding the collection enclosure and physically lowering the collection enclosure relative to the reaction chamber.

5. The method of claim 1, further comprising:
   housing the collection enclosure in a container filled with fluid; and
   oscillating the fluid level in the container up and down a number of times per minute.

6. The method of claim 1, further comprising:
   housing the collection enclosure in a container filled with fluid; and
   physically lowering the container relative to the reaction chamber.

7. The method of claim 5, further comprising decreasing and increasing the height of the fluid level in the container by three centimeters per minute.

8. The method of claim 5, further comprising oscillating the fluid level in the container from 10 to 30 times per minute.

9. The method of claim 1 wherein harvesting and preparing cells and tissue sections further comprises:
   removing cells resident on the tissue section to create a substantially acellular section; and
   plating the substantially acellular tissue section with the harvested cells.

10. The method of claim 1, wherein combining the cells and the tissue section in a culture medium further comprises:
    plating the tissue section with progenitor cells; and
    incubating the tissue section and progenitor cells in the bioreactor under environmental conditions appropriate for the tissue section to generate cell products.

11. The method of claim 1, wherein applying cyclic negative pressure to the culture further comprises:
    oscillating the culture medium over a period of time; and
    reducing the hydrostatic pressure on the collection enclosure relative to the hydrostatic pressure on the harvested tissue over the period of time, wherein the cell products collected move from a higher location to a lower location in the bioreactor.

12. The method of claim 1, wherein harvesting and preparing cells and tissue sections further comprises harvesting and preparing at least one of bone marrow extracellular matrix, stromal spindle cells, endothelial cells and progenitor cells.

13. The method of claim 1, wherein combining the cells and tissue sections further comprises:
    plating bone marrow extracellular matrix with at least one of stromal spindle cells and endothelial cells;
    incubating the extracellular matrix in culture medium; and
    plating the extracellular matrix with progenitor cells.

14. The method of claim 1, wherein collecting the cell products discharged further comprises collecting blood cells discharged.

15. The method of claim 1, further comprising providing substantially fresh culture media to cells in the collection enclosure over time.

16. A method for operating a bioreactor system for growing cells, wherein the bioreactor system includes a reaction chamber with a diffusion chamber for cultivating tissue and a collection enclosure connected to the diffusion chamber and associated with a hydrodynamic apparatus, the method comprising:
    placing harvested tissue and cells in the diffusion chamber in a cell culture medium;
    creating an oscillating negative pressure differential between the diffusion chamber and the collection enclosure over a period of time, wherein the oscillating negative pressure differential creates an environment suitable for collection of cell products in the collection enclosure; and
    collecting cell products in the collection enclosure.

17. The method of claim 16, wherein the diffusion chamber exchanges fluid and cell products with the collection enclosure through tubing connecting the diffusion chamber and the collection enclosure.

18. The method of claim 17, further comprising drawing cell culture medium through pores in the diffusion chamber to move cell products generated through the tubing and into the collection enclosure.

19. The method of claim 16, wherein creating an oscillating negative pressure differential further comprises creating oscillations in the culture medium within the collection enclosure.

20. The method of claim 16, wherein creating an oscillating negative pressure differential further comprises reducing hydrostatic pressure on the collection enclosure relative to the diffusion chamber to generate a negative pressure differential between the collection enclosure and the diffusion chamber.

21. The method of claim 17, wherein the hydrodynamic apparatus further comprises a cyclic container and a collection container which exchange fluid through tubing connecting the collection container and the cyclic container, the collection container housing the collection enclosure, the collection container and the cyclic container being positioned at original heights at start of an operational run of the bioreactor system, wherein creating the oscillating negative pressure over time further comprises:
    lowering the hydrodynamic apparatus relative to the reaction chamber during the operational run; and
    oscillating the cyclic container relative to the collection container during the operational run.

22. The method of claim 21, further comprising:
    adding cell culture medium to the reaction chamber intermittently over time; and
    repositioning the collection container and the cyclic container to the original heights, wherein the adding and repositioning steps allow continuation of the operational run over an additional period of time.

23. The method of claim 16, wherein the tissue in the reaction chamber is hematopoietic tissue and the cell products collected in the collection enclosure are blood cells.

* * * * *